(12) United States Patent
Hollauf et al.

(10) Patent No.: US 10,408,807 B2
(45) Date of Patent: Sep. 10, 2019

(54) METHOD FOR DETERMINING THE NH₃ LOADING OF AN SCR CATALYTIC CONVERTER

(75) Inventors: Bernd Hollauf, Graz (AT); Bernd Breitschaedel, Graz (AT)

(73) Assignee: AVL List GmbH, Graz (AT)

( * ) Notice: Subject to any disclaimer, the term of this patent is extended or adjusted under 35 U.S.C. 154(b) by 1102 days.

(21) Appl. No.: 13/991,166

(22) PCT Filed: Nov. 28, 2011

(86) PCT No.: PCT/EP2011/071144
§ 371 (c)(1),
(2), (4) Date: Aug. 2, 2013

(87) PCT Pub. No.: WO2012/072566
PCT Pub. Date: Jun. 7, 2012

(65) Prior Publication Data
US 2013/0332086 A1    Dec. 12, 2013

(30) Foreign Application Priority Data

Dec. 1, 2010    (AT) .................................... 1998/2010

(51) Int. Cl.
| | | |
|---|---|---|
| *F01N 3/00* | (2006.01) | |
| *G01N 33/00* | (2006.01) | |
| *F01N 3/20* | (2006.01) | |
| *F01N 9/00* | (2006.01) | |
| *F01N 11/00* | (2006.01) | |

(52) U.S. Cl.
CPC ......... *G01N 33/0004* (2013.01); *F01N 3/208* (2013.01); *F01N 9/005* (2013.01); *F01N 11/00* (2013.01); *F01N 2550/02* (2013.01); *F01N 2560/026* (2013.01); *F01N 2570/18* (2013.01); *F01N 2610/02* (2013.01); *F01N 2900/1402* (2013.01); *F01N 2900/1616* (2013.01); *F01N 2900/1622* (2013.01); *Y02T 10/24* (2013.01); *Y02T 10/47* (2013.01)

(58) Field of Classification Search
USPC ............................................... 60/286
See application file for complete search history.

(56) References Cited

U.S. PATENT DOCUMENTS

| | | | |
|---|---|---|---|
| 5,800,793 A | 9/1998 | Cole | |
| 2007/0204600 A1* | 9/2007 | Kubinski | ........... B01D 53/9431 60/286 |

FOREIGN PATENT DOCUMENTS

| | | |
|---|---|---|
| DE | 10347131 A1 | 5/2004 |
| DE | 10347130 A1 | 6/2004 |
| DE | 10347132 A1 | 6/2004 |
| DE | 102005050709 A1 | 4/2007 |
| DE | 102007040439 A1 | 3/2009 |

\* cited by examiner

*Primary Examiner* — Lam S Nguyen
(74) *Attorney, Agent, or Firm* — Jordan IP Law, LLC; Todd A. Vaughn

(57) ABSTRACT

A method for determining the NH₃ loading of an SCR catalytic converter in the exhaust-gas section of an internal combustion engine, in which the NH₃ concentration in the exhaust gas is determined by way of at least one sensor, preferably an NO$_x$ sensor, downstream of the SCR catalytic converter.

2 Claims, No Drawings

METHOD FOR DETERMINING THE NH₃ LOADING OF AN SCR CATALYTIC CONVERTER

CROSS-REFERENCE TO RELATED APPLICATIONS

The present application is a National Stage Application of PCT International Application No. PCT/EP2011/071144 (filed on Nov. 28, 2011), under 35 U.S.C. § 371, which claims priority to Austrian Patent Application No. A 1998/2010 (filed on Dec. 1, 2010), which are each hereby incorporated by reference in their respective entireties

TECHNICAL FIELD

The invention relates to a method for determining the $NH_3$ loading of an SCR catalytic converter in the exhaust-gas section of an internal combustion engine, wherein the $NH_3$ concentration in the exhaust gas is determined by way of at least one sensor, preferably an $NO_x$ sensor, downstream of the SCR catalytic converter.

BACKGROUND

Methods for the model-based control of an SCR catalytic converter of an internal combustion engine are known from the publications DE 10 347 130 A1, DE 10 347 131 A1 and DE 10 347 132 A1, wherein the respectively used dynamic model considers the $NH_3$ loading of the SCR catalytic converter. A modelled $NO_x$ value of the dynamic model will be adjusted continuously by means of an $NO_x$ value measured by an $NO_x$ sensor arranged downstream of the SCR catalytic converter.

Dynamic filling level models for SCR control are based on a model of the SCR catalytic converter which models the current $NH_3$ loading of the catalytic converter on the basis of mass balances. As a result of imprecisions in the sensor and actuator systems, this modelled $NH_3$ loading can drift away from the real value during operation, which is why the modelled $NH_3$ loading needs to be adjusted to the real loading in specific intervals.

SUMMARY

It is the object of the invention to improve the precision of filling level models in a simple way.

This is achieved in accordance with the invention in such a way that the current $NH_3$ filling level of the SCR catalytic converter is calculated directly via the dynamic equilibrium between $NH_3$ adsorption and $NH_3$ desorption on the basis of a measured $NH_3$ concentration downstream of the SCR catalytic converter, wherein at least one physical model based on adsorption isotherms is preferably used to determine the dynamic equilibrium.

DESCRIPTION

For the purpose of model adjustment, it is necessary at first to know or detect by means of measuring instruments the filling level of the SCR catalytic converter or the $NH_3$ concentration after the SCR catalytic converter. This can occur in different ways, e.g. by direct measurement by means of an $NH_3$ sensor or by utilising the cross-sensitivity of conventional $NO_x$ sensors to $NH_3$— via an $NO_x$ sensor.

Methods are known in literature in order to enable the reliable detection of $NH_3$, e.g. in propulsion operation (see DE 10 20 505 0709 A1).

If the $NH_3$ concentration after the real SCR catalytic converter is known, the static $NH_3$ filling level in the SCR catalytic converter can subsequently be calculated analytically via an adsorption isotherm.

It is preferably provided in this process that a Langmuir adsorption isotherm in the form of $$\Theta_{NH3} = \frac{K_A \cdot C_{NH3}}{1 + K_A \cdot C_{NH3}}$$

is used as an adsorption isotherm, wherein $\Theta_{NH3}$ is the current $NH_3$ loading, $K_A$ the adsorption equilibrium constant and $C_{NH3}$ the concentration of the component $NH_3$ in the exhaust gas downstream of the SCR catalytic converter. The adsorption equilibrium constant $K_A$ can be determined from characteristic maps or characteristic curves. If parameters for the reaction kinetics of the adsorption and desorption are known, the adsorption equilibrium constant $K_A$ can also be calculated by means of the same from the equation:

$$K_A = \frac{k_{ad} \cdot e^{-\frac{E_{ad}}{T_c}}}{k_{de} \cdot e^{-\frac{E_{de}}{T_c}}}$$

wherein $k_{ad}$ [m/s] is a pre-exponential term for the adsorption and $k_{de}$ [m/s] a pre-exponential term for the desorption, $E_{ad}$ [J/kmol] the activation energy for the adsorption, and $E_{de}$ [J/kmol] the activation energy for the desorption.

A BET isotherm in the form of:

$$\Theta_{NH3} = \frac{K \cdot q_{max} \cdot C_{NH3}}{(C_{sat} - C_{NH3}) \cdot \left[1 + \frac{(K-1) \cdot C_{NH3}}{C_{sat}}\right]}$$

can also be used as adsorption isotherm $\Theta_{NH3}$ as an alternative to the Langmuir adsorption isotherm, wherein $\Theta_{NH3}$ is the current $NH_3$ loading, $K$ the adsorption coefficient, $q_{max}$ the maximum concentration of the $NH_3$ in a layer at the surface of the exhaust gas, $C_{sat}$ the solubility of the $NH_3$, and $C_{NH3}$ the concentration of the component $NH_3$ in the exhaust gas downstream of the SCR catalytic converter.

It is further also possible to use a Freundlich isotherm in the form of:

$$\Theta_{NH3} = K_f \cdot C_{NH3}^n$$

as an adsorption isotherm, wherein $\Theta_{NH3}$ is the current $NH_3$ loading, $K_f$ the Freundlich coefficient, $C_{NH3}$ the concentration of the $NH_3$ in the exhaust gas downstream of the SCR catalytic converter, and $n$ the Freundlich exponent.

The described method allows a rapid and precise adjustment of the $NH_3$ filling level of the model to the real system (static method). Robust control is realised in this manner, which can achieve high $NO_x$ turnovers in combination with low $NH_3$ slippage at the SCR catalytic converter. This allows significantly improving the precision of dynamic filling level models.

What is claimed is:

1. A method for determining the $NH_3$ loading of an SCR catalytic converter in the exhaust-gas section of an internal combustion engine, comprising:

measuring an $NH_3$ concentration in the exhaust gas downstream of the SCR catalytic converter;

calculating a current $NH_3$ filling level of the SCR catalytic converter via a dynamic equilibrium between $NH_3$ adsorption and $NH_3$ desorption on a basis of a Langmuir adsorption isotherm that includes the measured $NH_3$ concentration downstream of the SCR catalytic converter and an adsorption equilibrium constant $K_A$; and adjusting a dynamic $NH_3$ filling level model to a static $NH_3$ loading based on the calculation.

2. The method according to claim 1, wherein the adsorption equilibrium constant $K_A$ is determined via characteristic maps or characteristic curves.

\* \* \* \* \*